US009884001B2

(12) United States Patent
Kim (10) Patent No.: US 9,884,001 B2
(45) Date of Patent: Feb. 6, 2018

(54) BOTULINUM TOXIN IN AEROSOL FORM AND METHOD OF FACIAL CONTOURING USING THE SAME

(71) Applicant: Sang Duck Kim, Seoul (KR)

(72) Inventor: Sang Duck Kim, Seoul (KR)

(73) Assignee: Sang Duck Kim, Seoul (KR)

( * ) Notice: Subject to any disclaimer, the term of this patent is extended or adjusted under 35 U.S.C. 154(b) by 0 days.

(21) Appl. No.: 14/821,584

(22) Filed: Aug. 7, 2015

(65) Prior Publication Data
US 2016/0038395 A1 Feb. 11, 2016

Related U.S. Application Data

(60) Provisional application No. 62/034,731, filed on Aug. 7, 2014.

(51) Int. Cl.
| | | |
|---|---|---|
| *A61K 8/04* | (2006.01) | |
| *A61K 8/66* | (2006.01) | |
| *A61Q 19/00* | (2006.01) | |
| *A61K 8/64* | (2006.01) | |
| *A61Q 19/08* | (2006.01) | |
| *A61K 8/19* | (2006.01) | |

(52) U.S. Cl.
CPC .............. *A61K 8/66* (2013.01); *A61K 8/046* (2013.01); *A61K 8/19* (2013.01); *A61K 8/64* (2013.01); *A61Q 19/00* (2013.01); *A61Q 19/08* (2013.01); *A61K 2800/22* (2013.01); *A61K 2800/74* (2013.01); *A61K 2800/91* (2013.01)

(58) Field of Classification Search
None
See application file for complete search history.

(56) References Cited

U.S. PATENT DOCUMENTS

| | | | | |
|---|---|---|---|---|
| 9,050,337 B2* | 6/2015 | Kim | ............... | A61K 38/4893 |
| 2008/0003242 A1* | 1/2008 | First | ............... | A61K 38/4893 |
| | | | | 424/239.1 |
| 2016/0106653 A1* | 4/2016 | Kim | ............... | A61K 38/4893 |
| | | | | 424/94.67 |

OTHER PUBLICATIONS

Discussion of the Anatomy of SMAS, Platysma and the Facial Nerve.
Broughton, M., The Superficial Musculoaponeurotic System of the Face: A Model Explored, Anatomy Research International, Sep. 10, 2013, pp. 1-5, vol. 2013, Hindawi Publis.
Prendergast, P., Anatomy of the Face and Neck, Cosmetic Surgery Art and Techniques, 2013, pp. 29-45, Springer-Verlag Berlin Heidelberg 2012.

* cited by examiner

*Primary Examiner* — Ralph J Gitomer
(74) *Attorney, Agent, or Firm* — DLA Piper LLP (US)

(57) ABSTRACT

The present invention provides a composition for facial contouring, comprising a mixture of botulinum toxin and air, and a method of facial contouring using the same. When the mixture of botulinum toxin and air is injected into an SMAS layer, the mixture strengthens the SMAS layer and draws back the galea aponeurotica to effectively lift up the face or change the facial contour, thus effectively enhancing the effect of facial contouring.

9 Claims, 8 Drawing Sheets

BOTULINUM TOXIN IN AEROSOL FORM AND METHOD OF FACIAL CONTOURING USING THE SAME

CROSS-REFERENCE TO RELATED PATENT APPLICATION

This application claims the benefit of U.S. provisional patent application No. 62/034,731, filed on Aug. 7, 2014, the disclosure of which is incorporated herein in its entirety by reference.

BACKGROUND OF THE INVENTION

1. Field of the Invention

The present invention relates to a composition for facial contouring, comprising a mixture of botulinum toxin and air, and a method of facial contouring using the same.

2. Description of the Related Art

In the human musculoskeletal system, each muscle including origin and insertion points is originated from a bone and attached to another bone, and thus the muscles control the movement of the musculoskeletal system by their movement. Meanwhile, unlike the body's musculoskeletal system, facial muscles are originated from the facial skeleton and attached to the skin to make facial expressions. Facial skin consists of several different layers, and each with a specialized function. The major skin layers include the epidermis, the dermis, and the hypodermis. A very thin fibromuscular layer, which is known as the superficial muscular aponeurotic system (hereinafter referred to as SMAS), is present between the subcutaneous fat layer and the muscular layer under the hypodermis, and all the fascia of the muscles of facial expression, the facial ligaments, and the subcutaneous fibrous tissues are fused to form a single thin layer over the face and the head. Histological observation of the SMAS layer shows that there are fibroblasts, myocytes, collagen, elastin, polysaccharides, etc. Therefore, the SMAS layer serves to uniformly connect whole facial muscles to the dermis and, at the same time, has a membrane structure distributed over the face and the head to connect various facial muscles to allow several muscles to make one facial expression in an integrated fashion. The SMAS layer becomes thinner with age, which makes wrinkles and causes the skin to sag. In general, the lifting procedure is performed to improve the sagging of the face by incising, pulling, and suturing the SMAS layer, but it causes side effects caused by anesthesia for surgery, side effects such as scars after surgery, and disturbance of daily life after surgery.

Botulinum toxin (also known as botulin toxin or botulinum neurotoxin) is a neurotoxin produced by the gram-positive bacteria *Clostridium botulinum*. Botulinum toxin produces paralysis of muscles by preventing synaptic transmission or release of acetylcholine across the neuromuscular junction and is thought to act in other ways as well. Botulinum toxin essentially blocks signals that normally would cause muscle spasms or contractions, resulting in paralysis. Botulinum toxin is classified into eight neurotoxins that are serologically related, but distinct. Of these, seven can cause paralysis, namely botulinum neurotoxin serotypes A, B, C, D, E, F and G. Among others, serotypes A and B are clinically used for the treatment of various diseases and wrinkles. Each of these is distinguished by neutralization with type-specific antibodies. Nonetheless, the molecular weight of the botulinum toxin protein, for all seven of these active botulinum toxin serotypes, is about 150 kD. The botulinum toxin secreted by bacteria is complexes comprising the 150 kD botulinum toxin protein molecule along with associated non-toxin proteins. The botulinum toxin type A complex can be produced by *Clostridium* bacteria as 900 kD, 500 kD and 300 kD forms. Botulinum toxin types B and C are apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg, about 12 times the primate LD50 for type A. Due to the molecular size and molecular structure of botulinum toxin, it cannot cross the stratum corneum and the multiple layers of the underlying skin architecture.

Botulinum toxin type A is said to be the most lethal natural biological agent known to man. Spores of *C. botulinum* are found in soil and can grow in improperly sterilized and sealed food containers. Ingestion of the bacteria can cause botulism, which can be fatal.

Meanwhile, facial contouring is a procedure to correct the facial contour by adjusting facial bones, and a method of cutting bones using a bone cutting saw has been conventionally used for the facial contouring. However, according to this method, a large bone should be cut, and a large amount of bones is cut at a time, which has a problem of accuracy. Therefore, in order to accurately determine the cutting angle, easily remove bone fragments, and facilitate the access to the cutting site, it is necessary to ensure the visibility, which requires large incision area, resulting in various problems such as severe swelling, severe bleeding, delayed healing, cut vessels, damaged nerves, etc. Moreover, the bone cutting saw may cause severe injury to the surrounding soft tissues during operation.

Moreover, for the same purpose, there is a method of using a file in which an adaptor with a converting mechanism for converting rotational motion to rectilinear motion is coupled to a powered surgical handpiece, a cutting element such as a file is coupled to the adaptor, an inlet is formed on the cutting surface of the file, a suction tube is coupled to the inlet, and the cutting element formed on an end of an elongated shaft is inserted into skin to cut bones for facial contouring. This method can solve various problems that may occur when the bone cutting saw is used, but cannot be effectively used in most bone cutting procedures performed using conventional saws such as facial contouring for angular chins or collection of bones for transplantation.

Meanwhile, the muscle-paralyzing effects of botulinum toxin have been used for therapeutic effects on various conditions such as hemifacial spasm, adult onset spasmodic torticollis, anal fissure, blepharospasm, cerebral palsy, cervical dystonia, migraine headaches, strabismus, temporomandibular joint disorder, and various types of muscle cramping and spasms. More recently, the muscle-paralyzing effects of botulinum toxin have been used in therapeutic and cosmetic facial applications such as treatment of wrinkles, frown lines, and other results of spasms or contractions of facial muscles. However, no method of facial contouring using botulinum toxin has been reported.

Accordingly, the present inventors have studied the applicability of botulinum toxin, which has been used for the treatment of various diseases, to existing methods of facial contouring and found that when the SMAS layer is selectively paralyzed by injecting a mixture of botulinum toxin and air into the SMAS layer, the mobility of untreated adjacent SMAS layer is strengthened, which in turn draw back the galea aponeurotica to effectively lift up the face or change the facial contour, which provides an enhanced effect of facial contouring, thus completing the present invention.

SUMMARY OF THE INVENTION

The present invention has been made in an effort to solve the above-described problems associated with prior art, and an object of the present invention is to provide a composition for facial contouring, comprising a mixture of botulinum toxin and air, and a method of facial contouring using the same.

To achieve the above object, the present invention provides a composition for facial contouring, comprising a mixture of botulinum toxin and air.

Moreover, the preset invention provides a method of facial contouring, comprising injecting the mixture into a superficial muscular aponeurotic system (SMAS) layer.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, preferred embodiments of the present invention will be described in detail with reference to the accompanying drawings.

The present invention provides a composition for facial contouring, comprising a mixture of botulinum toxin and air.

In the present invention, the term "botulinum toxin" refers to a molecule that has the biological activity of botulinum toxin and may be a protein, polypeptide, peptide, fusion protein, truncated protein, chimeric protein, mutant protein, or recombinant protein.

The biological activity of the toxin refers, within the context of the present invention, to muscular paralysis or inhibition of exocytosis, in particular, inhibition of exocytosis of acetylcholine or other neurotransmitters.

Pure or substantially pure botulinum neurotoxin can be obtained from a protein complex containing botulinum toxin, for example, according to the method described in the literature (Current topics in Microbiology and Immunology (1995), 195, p. 151-154). Pure or substantially pure botulinum neurotoxin can be obtained, for example, by purification of a fermentation medium or culture broth containing *Clostridium botulinum* and can be enriched, for example, with meat or protein-rich food.

The botulinum toxin may comprise at least one selected from the group consisting of botulinum toxin serotypes A, B, C, D, E, F and G, preferably botulinum toxin serotype A or B. The botulinum toxin may comprise both commercially available Dysport® and Botox®, botulinum neurotoxin Type A, without limitation. Moreover, commercially available Myobloc®, botulinum toxin Type B, may be included in the botulinum toxin.

The botulinum toxin and air may be mixed in a volume ratio of 1:0.1 to 1:20, preferably in a volume ratio of 1:10.

The composition of the present invention may be used in various forms for facial contour and may be injected into a superficial muscular aponeurotic system (SMAS) layer.

As used herein, the term "superficial muscular aponeurotic system (SMAS)" refers to a tough muscular layer under the facial skin, which is located about 4.5 mm from the skin between the subcutaneous fat layer and the muscular layer. The SMAS has a structure in which some thin layer of muscular fascia connects to fibrous septa of the subcutaneous tissue to deliver the movement of facial muscles to the skin, and thus is also known as the muscles of facial expression. With age, the SMAS layer is weakened and pulled down by gravity, causing wrinkles.

Figure 1:
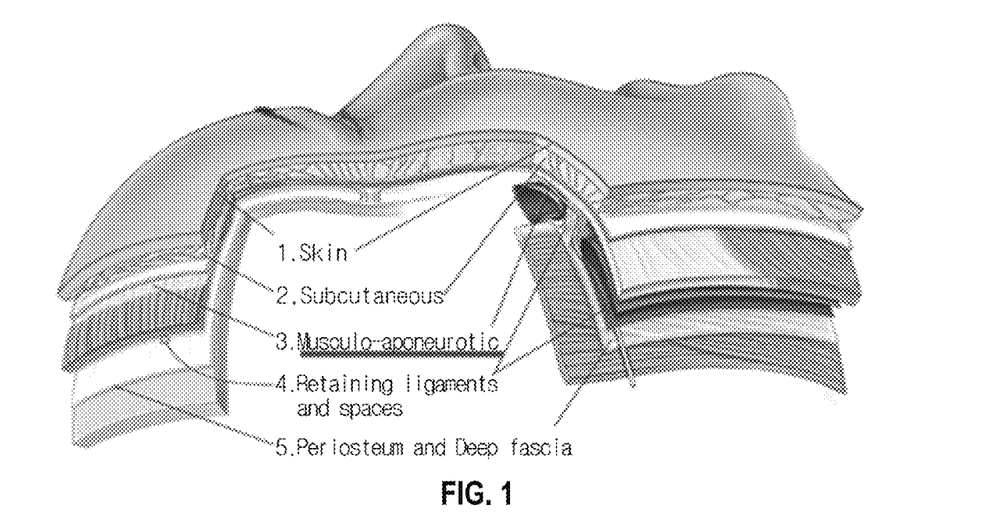
FIG. 1 is a diagram showing the SMAS layer.

As shown in FIG. 1, the SMAS may be imagined as a thin plastic bag covering the entire head, composed of thin muscle fibers of the facial muscles. The SMAS has an obvious layer in the outer part of the face. However, the layer becomes obscure in the inner part of the face and is absent in the center of the face such as perioral area. The network of the SMAS acts as a distributor of force for various facial muscles, and thus a blended smooth expression of the face is made.

Figure 2:
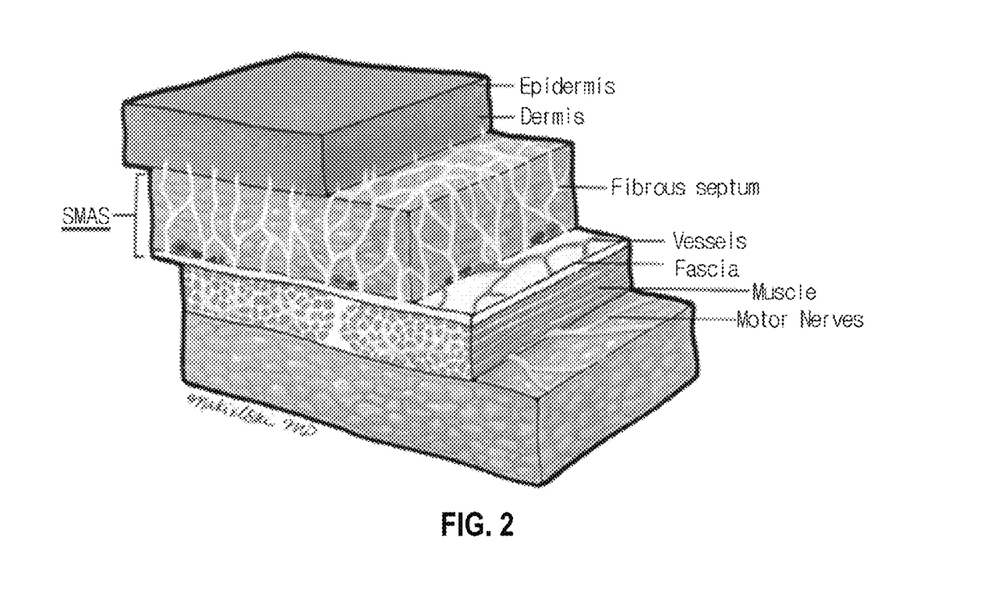
FIG. 2 is a diagram showing an effect caused by injection of a composition of the invention into the SMAS.

When the composition of the present invention is injected into a specific plane of the SMAS, it partially paralyzes the SMAS, strengthens the contraction of adjacent SMAS to adjust the equilibrium point of the whole SMAS in a normal static state, which causes the movement or contraction of the SMAS, which in turn draws back the galea aponeurotica to lift up the scalp backwards as shown in FIG. 2.

As such, the effect of drawing back the galea aponeurotica lifts up the face or change the facial contour.

The composition of the present invention may further comprise appropriate carriers, excipients, and diluents which are generally used in the preparation of pharmaceutical compositions.

The composition of the present invention may preferably be formulated in the form of liquid, aerosol, and sterile injection, and most preferably, the mixture of botulinum toxin and air may be formulated in the form of aerosol. When the composition is formulated, diluents or excipients such as fillers, extenders, binders, wetting agents, disintegrants, surfactants, etc. may be used.

The composition of the present invention may optionally comprise a dispersant. As used herein, the dispersant refers to any substance or additive capable of preventing or minimizing undesired or uncontrolled agglomeration between the botulinum toxin and the carrier of the present invention. The dispersant is useful when a concentrated botulinum toxin solution is to be employed due to capacity limit, for example. In these cases, the dispersant allows the botulinum toxin to be dispersed, thus preventing the agglomeration of toxins which may occur in the absence of the dispersant. In general, the dispersant (1) is non-irritating, (2) does not destroy the botulinum toxin, (3) does not cause an increase in permeability, (4) has a reliable and stable particle size, (5) does not have a charge, and (6) does not interfere with complexes of toxins and transdermal carriers.

The injection of the present invention refers to the administration of a predetermined composition of the present invention to a subject by any suitable route.

The preferred dosage of the pharmaceutical composition of the present invention depends on the condition and weight of a patient, the severity of disease, the type of drug, the route and duration of administration, etc., but may be appropriately selected by those skilled in the art. For the desired effect, the composition of the present invention may be administered in an amount of 0.1 unit to 3000 units per injection, preferably 1 unit to 10 units, based on the content of botulinum toxin type A. The composition of the present invention may be administered once or several times a day.

The sites of administration of the composition of the invention are shown in FIGS. 3 to 6.

Figure 3:
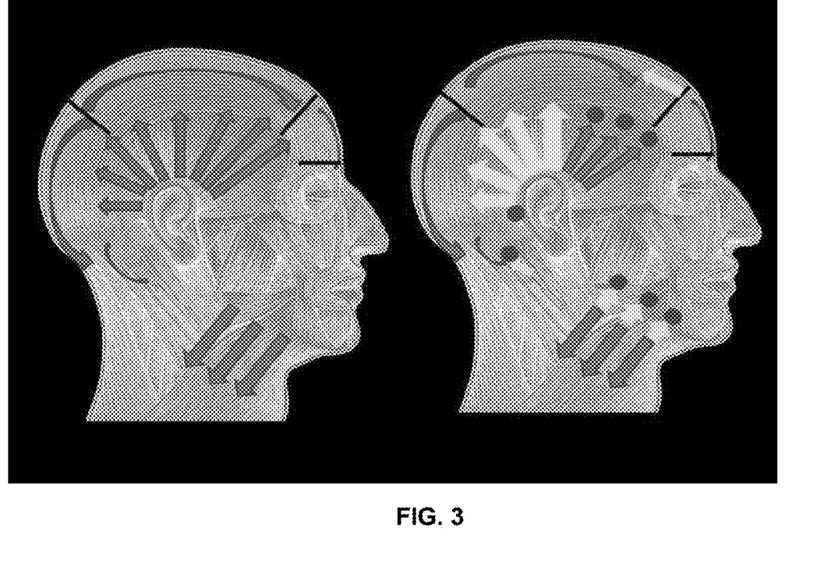
FIG. 3 is a diagram showing the sites of administration of the composition of the invention in a human head without facial movement.
Figure 4:
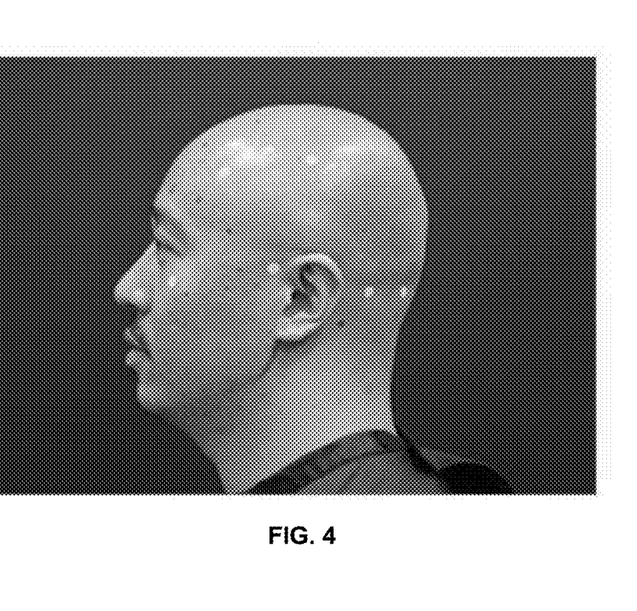
FIG. 4 is a diagram showing the sites of administration of the composition of the invention in a contracting state of the frontal belly.
Figure 5:
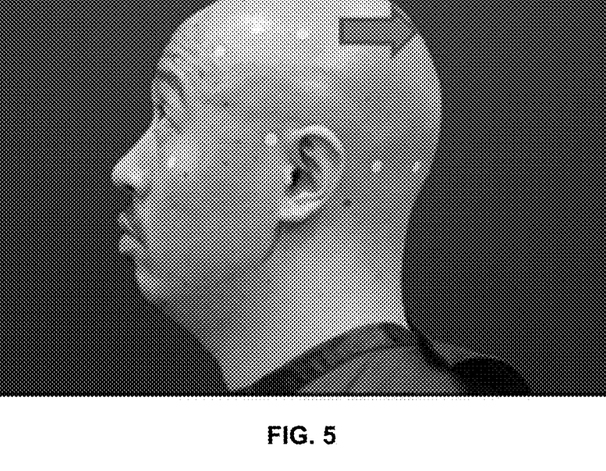
FIG. 5 is a diagram showing the sites of administration of the composition of the invention in a contracting state of the orbicularis oris and levator labii superioris muscles.
Figure 6:
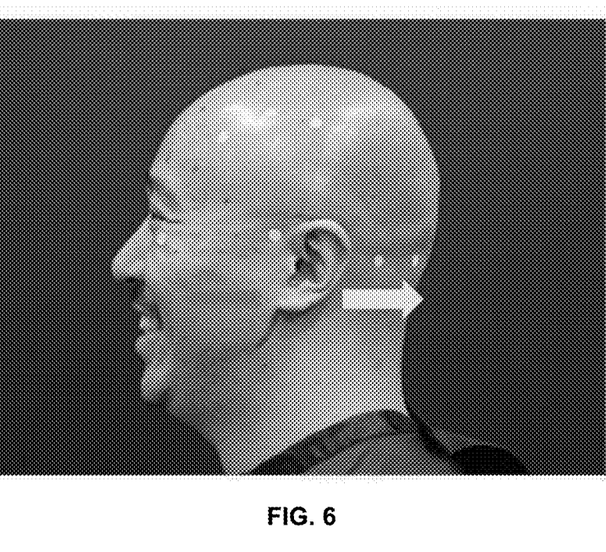
FIG. 6 is a diagram showing the sites of administration of the composition of the invention in a contracting state of the platysma where the facial skin drops down.
Figure 7:
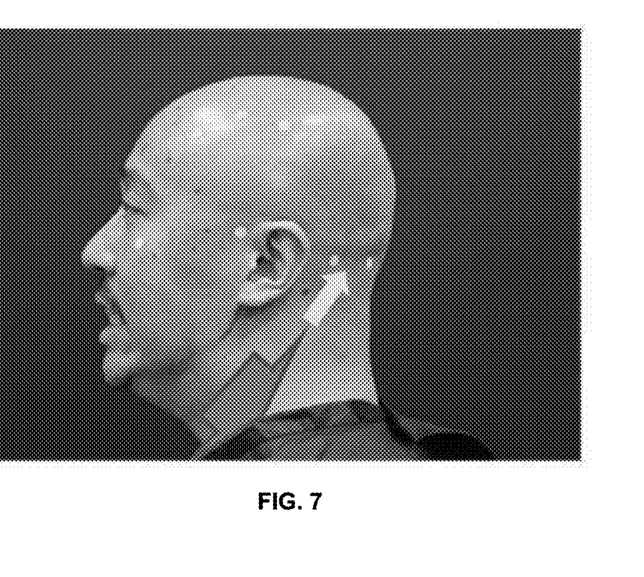
FIG. 7 is a diagram showing the change of facial contouring in patient A before and 6 months after the injection of the composition of the present invention.
Figure 8:
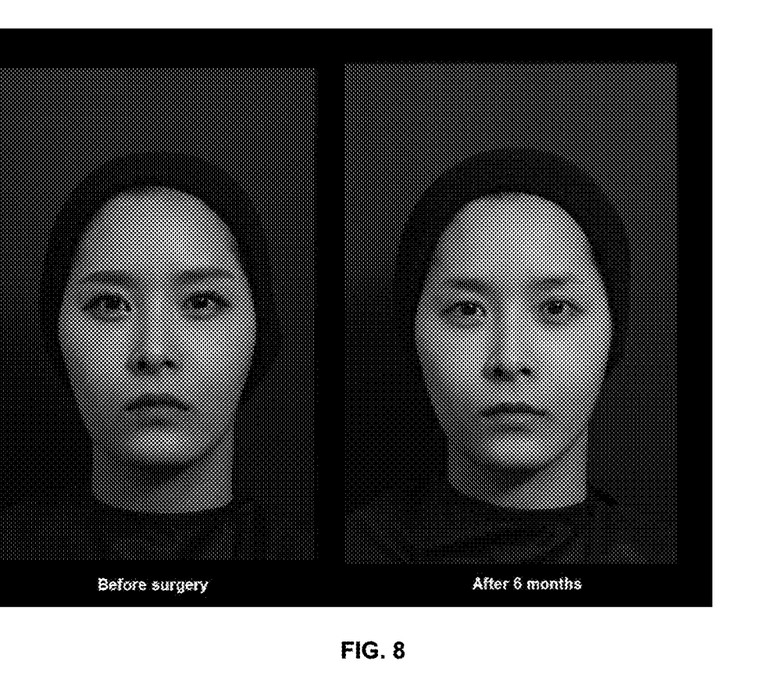
FIG. 8 is a diagram showing the change of facial contouring in patient B before and 4 weeks after the injection of the composition of the present invention.
Figure 9:
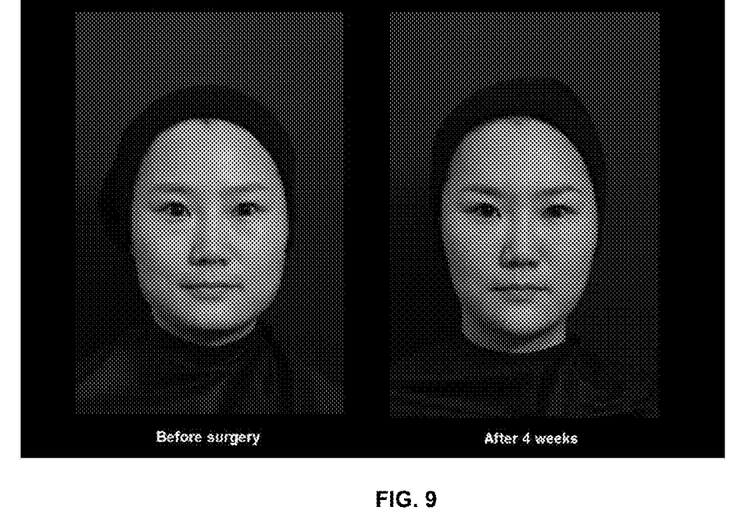
FIG. 9 is a diagram showing the change of facial contouring in patient C before and 2 weeks months after the injection of the composition of the present invention.
Figure 10:
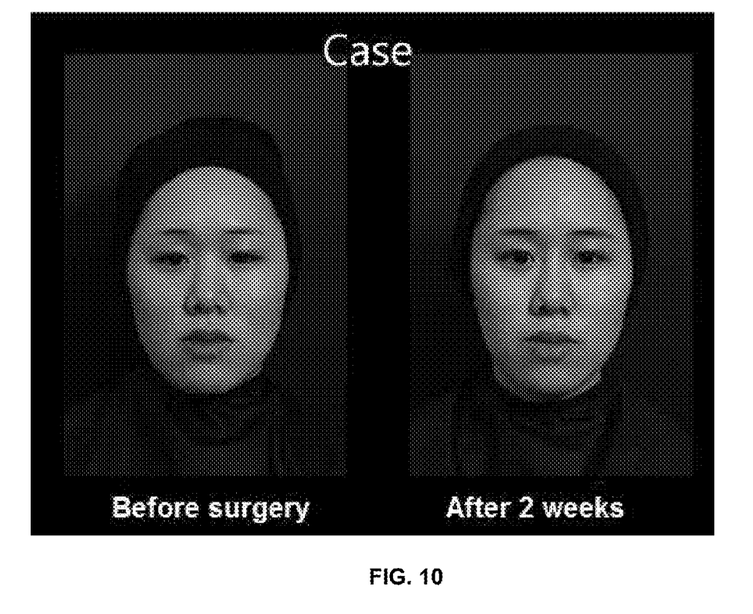
FIG. 10 is a diagram showing the change of facial contouring in patient D before and 2 weeks after the injection of the composition of the present invention.
Figure 11:
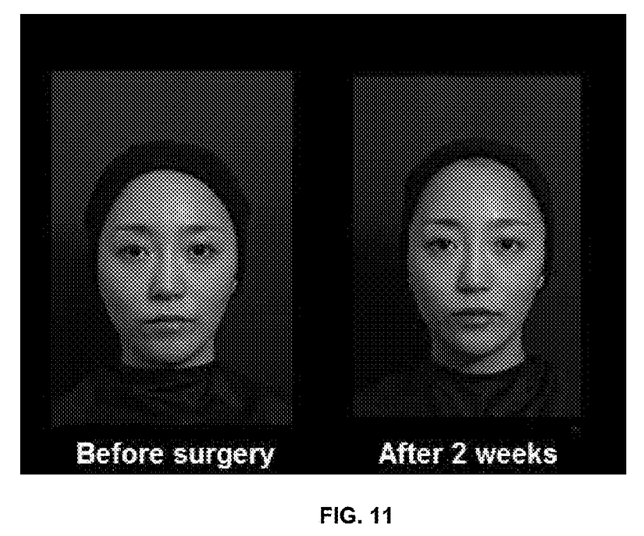
FIG. 11 is a diagram showing the change of facial contouring in patient E before and 4 weeks after the injection of the composition of the present invention.
Figure 12:
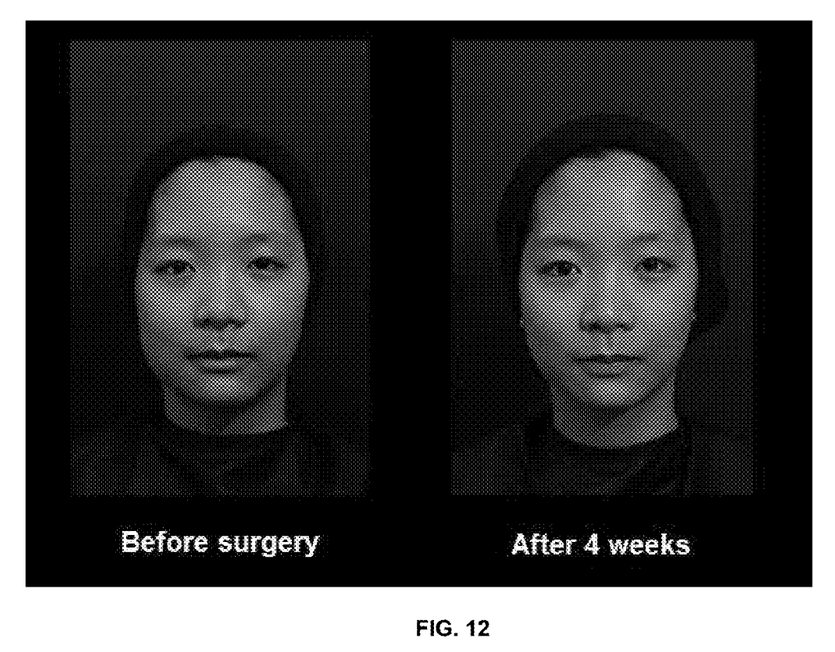
FIG. 12 is a diagram showing the change of facial contouring in patient F before and after the one-time injection of the composition of the present invention.
Figure 13:
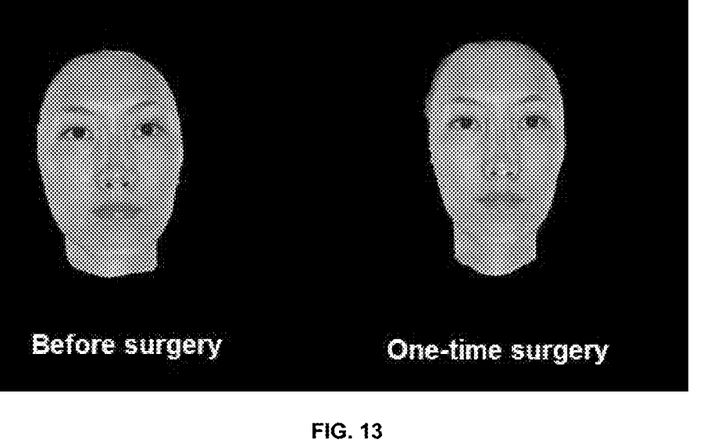
FIG. 13 is a diagram showing the change of facial contouring in patient G before and 1 month after the injection of the composition of the present invention.
Figure 14:
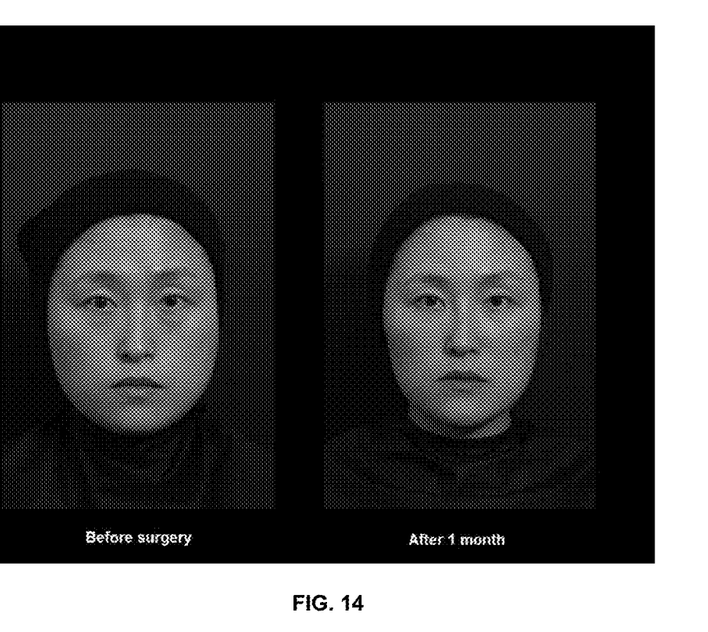
FIG. 14 is a diagram showing the change of facial contouring in a female patient (patient H) before and 1 month after the injection of the composition of the present invention.
Figure 15:
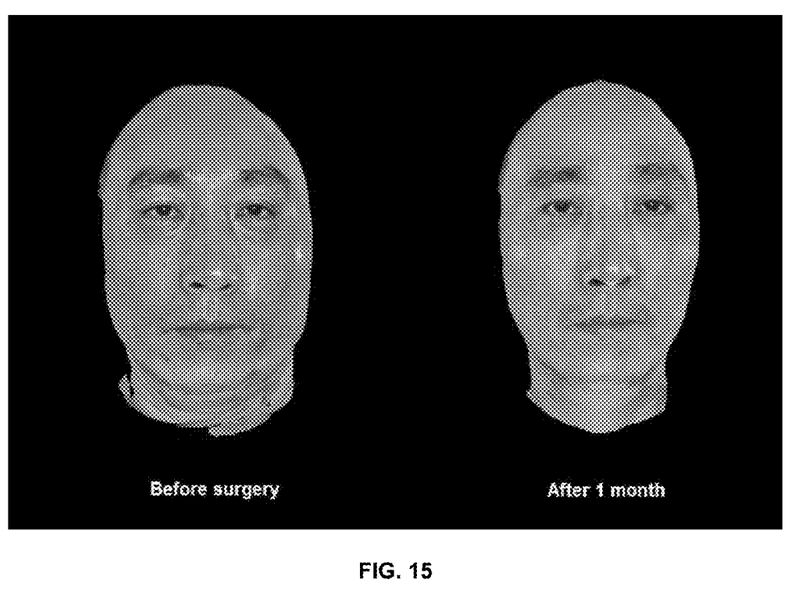
FIG. 15 is a diagram showing the change of facial contouring in a male patient (patient I) before and 1 month after the injection of the composition of the present invention.

FIG. 3 shows a human head without facial movement, FIG. 4 shows a contracting state of the frontal belly, FIG. 5 shows a contracting state of the orbicularis oris and levator labii superioris muscles, and FIG. 6 shows a contracting state of the platysma where the facial skin drops down.

As shown in FIG. 4, the skins marked with yellow spots and red spots are gathered in red posts just above the eyebrows. When the composition of the present invention is injected into three yellow spots in the immediate vicinity of the red spot, the contraction of the superficial fascia in the occipital region is strengthened, and as a result, the facial skin in the frontal region is pulled toward the occipital region, which in turn lifts up the entire upper face.

Moreover, as shown in FIG. 5, there are muscles that contract towards the occipital region in a direction opposite to the blue arrow indicating muscles that contract from the ear to the cheekbone, and when the composition of the present invention is injected into the yellow spots and red spots around the cheekbone, the contraction in the direction of the yellow arrow is strengthened, and thus the cheekbone is reduced.

Furthermore, as shown in FIG. 6, when the composition of the present invention is injected into the region along the red line indicating the jawline to selectively paralyze the platysma SMAS, the contraction of the SMAS is strengthened along the yellow spots in the occipital region, and as a result, the lower face is reduced, exhibiting the lifting effect.

The composition of the present invention may be used alone or in conjunction with surgery, radiation therapy, hormone therapy, chemical therapy, and methods using biological response modifiers for facial contouring.

Moreover, the present invention provides an aerosol spray kit comprising the composition formulated in the form of aerosol.

The aerosol form can control the spread of botulinum toxin to limit its effects on cut planes. Moreover, aerosol form can deliver a tiny amount of botulinum toxin to the target SMAS to adjust the tug-of-war between muscle fibers in SMAS.

The present invention provides a kit comprising a device for injecting the botulinum toxin into the skin and a carrier as well as a liquid, gel, cream, etc. suitable for use in the skin or epithelium of a subject. The kit for administration of the composition of the present invention under the instructions of a medical practitioner or by a patient or subject may comprise a custom applicator suitable for that purpose.

Moreover, the present invention provides a method of facial contouring, comprising injecting a mixture of botulinum toxin and air into a superficial muscular aponeurotic system (SMAS) layer.

In the above step, when the mixture of botulinum toxin and air is injected into the SMAS layer, the mixture draws back the galea aponeurotica to effectively lift up the face or change the facial contour.

The botulinum toxin and air may be mixed in a volume ratio of 1:0.1 to 1:20, preferably in a volume ratio of 1:10.

The injection may be performed by administering the mixture to the SMAS layer through a 28-gauge to 31-gauge syringe needle, and the mixture may preferably be sprayed through a 31-gauge syringe needle and may be sprayed and injected into the SMAS layer at a very high pressure by Bernoulli's fluid dynamics. Moreover, a BD insulin syringe with a 28-gauge to 31-gauge syringe needle may be used.

The injection may preferably be performed by spraying the mixture in the form of aerosol.

Unlike conventional botulinum toxin injections that paralyze the target muscles, the method of facial contouring using the composition of the present invention can exhibit longer treatment duration lasting more than a year, because it partially paralyzes the muscles treated to induce strengthened untreated adjacent muscles, generating muscle tone shift. Accordingly, the method of the present invention can be an excellent substitute for various facial contouring procedures such as double jaw surgery, reduction mandibuloplasty, and reduction zygoplasty.

Hereinafter, the present invention will be described in detail with reference to Examples. However, the following Examples are merely illustrative of the present invention and the present invention is not limited by the following Examples.

Example 1: Preparation of Composition Comprising Mixture of Botulinum Toxin and Air A 0.5 U/cc botulinum toxin solution was prepared by adding 10 cc saline solution to a bottle containing 100 U Botox, botulinum toxin Type A. The prepared botulinum toxin solution was loaded in a BD Ultra-Fine™ II Short Needle Insulin Syringe 3/10 cc 31 G×8 mm (5/16 in), and air was drawn into the corresponding syringe to prepare a mixture of botulinum toxin and air in a volume ratio of 1:10 and 1:20, respectively.

Example 2: Determination of Effect of Facial Contouring

The effect of facial contouring was determined by injecting the composition in the form of aerosol prepared in Example 1 into the SMAS layer of each of eight patients (A to H). The appearance after the treatment was compared to that before the treatment, and the results are shown in FIGS. 7 to 15.

Cheekbones of patient A were reduced using a 1:10 mixture of allergan botox, botulinum toxin Type A, and face reduction and lifting surgery was performed on patient B using a 1:20 mixture of allergan botox.

1:10 mixtures, each comprising Dysport, Xeomin, Meditoxin, and BTX-A, botulinum toxin Type B, respectively, were used in patients C to F, and 1:10 and 1:20 mixtures of Myobloc, botulinum toxin Type, were used in patients G and H, respectively.

As shown in FIGS. 3 to 6, all of the patients subjected to the treatment of the present invention had the effect of facial contouring and, in particular, severe asymmetries of patients E and F were corrected by injecting the composition into the right face only.

In the following, formulation examples of the composition of the present invention will be illustrated.

Formulation Example 1: Pharmaceutical Composition 1.1 Preparation of Injection

| | |
|---|---|
| Mixture of botulinum toxin and air of the present invention | 10 mg |
| Mannitol | 180 mg |
| Sterile distilled water for injection | 2974 mg |
| Na$_2$HPO$_4$·2H$_2$O | 26 mg |

An injection is prepared with the above ingredients per ampoule (2 ml) according to a conventional method for preparing injections.

1.2 Preparation of Liquid Formulation

| | |
|---|---|
| Mixture of botulinum toxin and air of the present invention | 10 mg |
| Isomerized sugar | 10 g |
| Mannitol | 5 mg |
| Purified water | Proper quantity |

A liquid formulation is prepared according to a conventional method for preparing liquid formations by dissolving each ingredient in purified water, adding a proper quantity of lemon flavor, mixing the ingredients, adding purified water to the resulting mixture to regulate the total mixture to 100 ml, filling the mixture in a brown bottle, and sterilizing the mixture.

As described above, when the mixture of botulinum toxin and air the injection of is injected into the SMAS layer, the mobility of untreated adjacent SMAS layer is strengthened, and thus the SMAS layer contracts, which in turn draw back the galea aponeurotica to effectively lift up the face or change the facial contour, thus effectively enhancing the effect of facial contouring.

While the invention has been shown and described with reference to certain preferred embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

What is claimed is:

1. A method of facial contouring, comprising:
    administering a mixture of botulinum toxin and air formulated in an aerosol form into a superficial muscular aponeurotic system (SMAS) layer.

2. The method of facial contouring of claim 1, wherein the botulinum toxin and air are mixed in a volume ratio of 1:0.1 to 1:20.

3. The method of facial contouring of claim 1, wherein the administering of the mixture changes facial contour.

4. The method of facial contouring of claim 1, wherein the administering of the mixture comprises:
    injecting a first end of a delivery device into the SMAS layer; and
    applying a high pressure on a second end of the delivery device, while maintaining the first end of the delivery device in the SMAS layer, to spread the mixture in the form of aerosol into the SMAS layer.

5. The method of facial contouring of claim 4, wherein the delivery device is a syringe with a needle.

6. The method of facial contouring of claim 5, wherein the needle is 28-gauge or 31-gauge.

7. The method of facial contouring of claim 1, wherein the botulinum toxin is botulinum toxin serotype A or B.

8. The method of facial contouring of claim 5, wherein the first end of the delivery device is a needle.

9. The method of facial contouring of claim 5, wherein the second end of the delivery device is the plunger of the syringe.

* * * * *